US00PP15455P3

(12) United States Plant Patent
Faria

(10) Patent No.: US PP15,455 P3
(45) Date of Patent: Dec. 28, 2004

(54) *COREOPSIS* PLANT NAMED 'LIMEROCK RUBY'

(50) Latin Name: *Coreopsis rosea×Coreopsis verticillata*
Varietal Denomination: Limerock Ruby

(75) Inventor: Mary Ann Faria, Lincoln, RI (US)

(73) Assignee: Limerock Plant Farm, Inc., Lincoln, RI (US)

( * ) Notice: Subject to any disclaimer, the term of this patent is extended or adjusted under 35 U.S.C. 154(b) by 389 days.

(21) Appl. No.: 09/968,336

(22) Filed: Sep. 30, 2001

(65) Prior Publication Data

US 2003/0066114 P1 Apr. 3, 2003

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—June Hwu
(74) *Attorney, Agent, or Firm*—C. A. Whealy

(57) ABSTRACT

A distinct cultivar of *Coreopsis* plant named 'Limerock Ruby', characterized by its daisy-type inflorescences that are about 3.25 cm in diameter; unique dark crimson red-colored ray florets and dark purple-colored disc florets; very freely flowering habit with numerous inflorescences per plant; and upright and outwardly spreading growth habit.

1 Drawing Sheet

BACKGROUND OF THE INVENTION

The present invention relates to a new and distinct cultivar of *Coreopsis* plant, botanically known as *Coreopsis rosea*× *Coreopsis verticillata* and hereinafter referred to by the name 'Limerock Ruby'.

The new *Coreopsis* was discovered by the Inventor in a controlled environment in Lincoln, R.I. on Aug. 3, 1998, as a chance seedling from random cross-pollinations of unidentified selections of *Coreopsis rosea* and *Coreopsis verticillata*, not patented. The new *Coreopsis* was observed as a single plant in a group of flowering plants of the unidentified selections of *Coreopsis rosea* and *Coreopsis verticillata*. The selection of this plant was based on its unique ray and disc floret coloration.

Asexual reproduction of the new *Coreopsis* by divisions taken in a controlled environment in Lincoln, R.I. since Aug. 3, 1998, has shown that the unique features of this new *Coreopsis* are stable and reproduced true to type in successive generations.

SUMMARY OF THE INVENTION

The cultivar Limerock Ruby has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Limerock Ruby'. These characteristics in combination distinguish 'Limerock Ruby' as a new and distinct cultivar:

1. Daisy-type inflorescences that are about 3.25 cm in diameter.
2. Unique dark crimson red-colored ray florets and dark purple-colored disc florets.
3. Very freely flowering with numerous inflorescences per plant.
4. Upright and outwardly spreading growth habit.

Plants of the new *Coreopsis* differ from plants of the parent selections and other known cultivars of *Coreopsis rosea* and *Coreopsis verticillata* primarily in ray and disc floret coloration. Plants of selections and cultivars of *Coreopsis rosea* known to the Inventor, not patented, have yellow-colored ray and disc florets and plants of selections and cultivars of *Coreopsis verticillata* known to the Inventor, not patented, have pink-colored ray florets and yellow-colored disc florets.

BRIEF DESCRIPTION OF THE PHOTOGRAPH

The accompanying colored photograph illustrates the overall appearance of the new *Coreopsis,* showing the colors as true as it is reasonably possible to obtain in colored reproductions of this type. Colors in the photograph may differ slightly from the color values cited in the detailed botanical description which accurately describe the colors of the new *Coreopsis.* The photograph of Sheet 1 comprises a close-up view of typical inflorescences and leaves of 'Limerock Ruby'.

DETAILED BOTANICAL DESCRIPTION

In the following description, color references are made to The Royal Horticultural Society Colour Chart except where general terms of ordinary dictionary significance are used. The following observations and measurements describe pinched plants grown in Keller, Tex. during the summer and fall outdoors under full sun and cultural conditions which approximate commercial practice. Plants used for the photographs and descriptions were grown as single plants in one-gallon containers and were about 9 to 10 months old. Measurements and numerical values represent averages taken from a group of flowering plants.

Botanical classification: *Coreopsis rosea*×*Coreopsis verticillata* cultivar Limerock Ruby.

Parentage: Chance seedling from random cross-pollinations of unidentified selections of *Coreopsis rosea* and *Coreopsis verticillata*, not patented.

Propagation:

*Type.*—Terminal tip cuttings.

*Time to initiate roots.*—Summer: About 8 to 12 days at temperatures of 23 to 29° C. Winter: About 10 to 14 days at temperatures of 15 to 20° C.

*Time to produce a rooted cutting.*—Summer: About 35 to 45 days at temperatures of 23 to 29° C. Winter: About 45 to 50 days at temperatures of 15 to 20° C.

*Root description.*—Fine and well-branched.

Plant description:

*Appearance.*—Perennial; upright and outwardly spreading; mounding habit.

*Plant size.*—Height: About 39 cm. Diameter or spread: About 27 cm.

*Lateral branch description.*—Freely branching, usually two laterals will develop at every node. Pinching is not required, however plants tend to be sturdier and more upright if pinched. Aspect: Initially upright, then outwardly arching. Strength: Moderate; stems will start to arch with the weight of inflorescences. Length: About 33 cm. Diameter: About 2 mm. Internode length: About 4 cm. Texture: Smooth, glabrous. Color: Close to 146A.

*Foliage description.*—Arrangement: Opposite, single; sessile. Length: About 3.9 cm. Width: About 2.5 mm. Shape: Linear. Apex: Acute. Base: Attenuate. Texture: Smooth, glabrous. Color: Young and mature foliage upper surface: Between 147A and 146A. Young and mature foliage lower surface: Closest to 147B.

Flowering description:

*Appearance.*—Daisy-type inflorescence form with elongated oblong-shaped ray florets. Inflorescences borne on terminals, arising from leaf axils. Disc and ray florets arranged on acropetally on a capitulum. Inflorescences persistent.

*Flowering response.*—Under natural conditions, plant flower in the late spring after sufficient cool temperatures and continue to flower through the fall.

*Inflorescence longevity.*—Individual inflorescences last about one to two weeks.

*Quantity of inflorescences.*—Very freely flowering with more than 125 flower buds and inflorescences per plant.

*Inflorescence size.*—Diameter: About 3.25 cm. Depth (height): About 7 mm. Diameter of disc: About. 5.75 mm.

*Fragrance.*—Very faint; sweet, grass-like.

*Flower buds.*—Height: About 4 mm. Diameter: About 3.5 mm. Shape: Roughly spherical. Color: Tight bud, close to 148A; just before opening, apex, close to 187A.

*Ray florets.*—Shape: Elongated oblong. Length: About 1.5 cm. Width: About 7 mm. Apex: Emarginate; deeply incised; typically three teeth. Base: Attenuate. Corolla tube length: About 2.5 mm. Margin: Entire. Texture: Smooth, velvety, glabrous. Aspect: Initially upright; when mature, about 90° from vertical, perpendicular to peduncle; flat. Number of ray florets per inflorescence: About 8 arranged in a single row. Color: When opening and fully opened, upper surface: Richer and more intense than 59A to more red than 187A; iridescent. Color does not fade with subsequent development. When opening and fully opened, lower surface: Closest to 78A.

*Disc florets.*—Arrangement: Massed at the center of the inflorescence. Shape: Tubular, flared at apex. Length: About 3 mm. Width: Apex: About 1.5 mm. Base: About 1 mm. Number of disc florets per inflorescence: About 35. Color: Immature and mature: Apex: Close to 187B. Mid-section: Close to 9A. Base: Close to 155D.

*Peduncle.*—Strength: Very strong, wiry; flexible. Aspect: Mostly upright. Length: About 5.7 cm. Diameter: About 0.5 mm. Texture: Smooth, glabrous. Color: 146A.

*Involucral bracts.*—Quantity: About 8 arranged in one row; imbricate. Length: About 6.5 mm. Width: About 3 mm at the base. Shape: Ovate. Apex: Acute. Base: Attenuate. Texture: Smooth, waxy. Color, both surfaces: Towards base, between 146A and 148A; towards apex, close to 164A.

*Reproductive organs.*—Androecium: Present on disc florets only. Anther color: 15 A. Amount of pollen: Moderate. Pollen color: 24A. Gynoecium: Present on both ray and disc florets.

*Seed/fruit.*—Seed/fruit production has not been observed.

Disease/pest resistance: Resistance to pathogens and pests common to *Coreopsis* has not been observed on plants grown under commercial conditions.

Temperature tolerance: Plants of the new *Coreopsis* have demonstrated good tolerance to night temperatures as low as −20° C. and day temperatures as high as 42° C.

It is claimed:

1. A new and distinct cultivar of *Coreopsis* plant named 'Limerock Ruby', as illustrated and described.

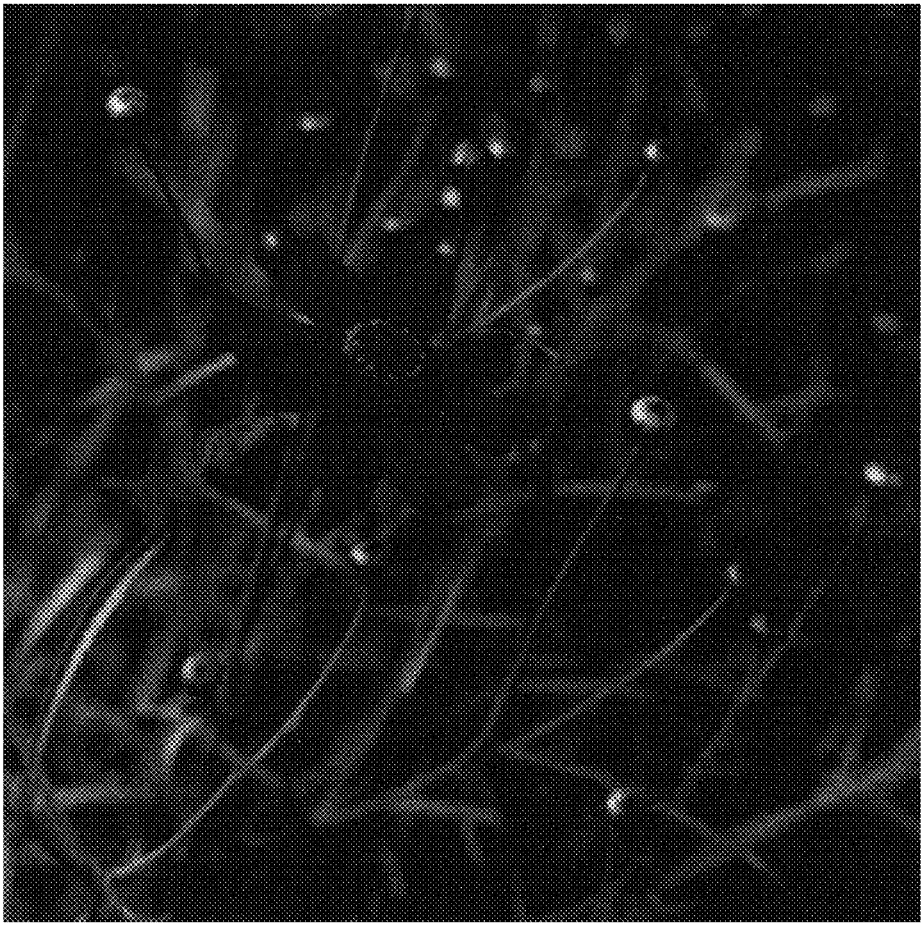

* * * * *